United States Patent [19]

Benson

[11] Patent Number: 5,489,531
[45] Date of Patent: Feb. 6, 1996

[54] COMBINED TWO STAGE METHOD FOR CLEANING AND DECONTAMINATING SURGICAL INSTRUMENTS

[75] Inventor: Leslee M. Benson, Collinsville, Ill.

[73] Assignee: E. R. Squibb and Sons, Inc., Princeton, N.J.

[21] Appl. No.: 919,519

[22] Filed: Jul. 24, 1992

Related U.S. Application Data

[63] Continuation-in-part of Ser. No. 597,651, Oct. 15, 1990, abandoned.

[51] Int. Cl.$^6$ ............................................. D06M 16/00
[52] U.S. Cl. ........................... 435/264; 134/26; 252/106; 252/174.12; 422/28
[58] Field of Search ................. 422/28, 37; 252/174.12, 252/106; 134/42, 26; 435/264

[56] References Cited

U.S. PATENT DOCUMENTS

| | | | |
|---|---|---|---|
| 3,860,528 | 1/1975 | Dewitt et al. | 252/182.18 |
| 3,928,223 | 12/1975 | Murray | 252/95 |
| 4,206,069 | 3/1980 | Borrello | 252/117 |
| 4,456,544 | 6/1984 | Lupova et al. | 435/264 |
| 4,477,361 | 10/1984 | Sperti et al. | 252/106 |
| 4,522,739 | 6/1985 | Gray | 252/99 |
| 4,566,985 | 1/1986 | Bruno et al. | 435/264 |
| 4,784,790 | 11/1988 | Disch et al. | 134/42 |
| 4,867,797 | 9/1989 | Thomasen et al. | 435/264 |
| 4,959,179 | 9/1990 | Aronson et al. | 252/135 |
| 5,089,163 | 2/1992 | Aronson et al. | 252/135 |

FOREIGN PATENT DOCUMENTS

| | | | |
|---|---|---|---|
| 2123194 | 5/1990 | Japan | 134/42 |

OTHER PUBLICATIONS

Seymour S. Block, *Disinfection, Sterilization, and Preservation*, 3rd Ed. (1983), pp. 481–482.
Calgon Vestal Laboratories Technical Bulletin: 92A–601 Dec. 1, 1986.
Calgon Vestal Laboratories Technical Data: Klenzyme Sep. 28, 1987.
Calgon Vestal Laboratories Technical Data: Vesta–Syde Interim Instrument Decontamination System Product Data Jan. 1991.
Calgon Vestal Laboratories Vesphene II se Technical Data: Jun. 1991.

*Primary Examiner*—Laura Collins
*Attorney, Agent, or Firm*—Theodore R. Furman, Jr.

[57] ABSTRACT

A two stage method using the same container for both cleaning and microbiologically decontaminating grossly soiled surgical instruments is described. A presoak in an enzyme solution is followed by direct addition of a compatible disinfectant and a continued soak to decontaminate surgical instruments and other paraphernalia used in healthcare facilities.

4 Claims, No Drawings

5,489,531

COMBINED TWO STAGE METHOD FOR CLEANING AND DECONTAMINATING SURGICAL INSTRUMENTS

REFERENCE TO RELATED APPLICATIONS

This application is a continuation-in-part of application Ser. No. 597,651, filed Oct. 15, 1990, now abandoned.

BACKGROUND OF THE INVENTION

1. Field of the Invention

The present invention is in the field of cleaning and decontaminating surgical instruments and other medical paraphernalia used in healthcare facilities. This cleaning and decontamination takes place as a preliminary step subsequent to use and soiling of the surgical instruments, and prior to their sterilization by autoclave.

Heretofore, it has been a common practice to merely place used surgical instruments and paraphernalia on towels or in a covered pan prior to their being sent to a central service facility for sterilization by autoclave, an apparatus which uses superheated steam under pressure to achieve total microbiological decontamination. Thus, no precautions have usually been taken to prevent the transmission of tissue and blood-borne diseases which may take place when personnel working with the soiled surgical instruments accidentally suffer cuts or punctures from these sharp instruments and thereby come in direct contact with blood and tissue on the soiled instruments. Because sterilization was being achieved in the autoclaving process, prior cleaning may have been carried out, but a disinfecting step was either carried out by a separate step or considered redundant, and therefore not used.

More recently, however, there has been widespread concern about the transmission of very serious and often fatal diseases, such as nosocomial infections from resistant strains of bacteria which commonly arise in healthcare facilities, and by viruses carried in tissues and blood, such as hepatitis B and HIV, which may be transmitted to personnel dealing with soiled surgical instruments, as described above.

But, it has been difficult to achieve microbiological decontamination by a method that is vigorous enough to kill resistant strains of *Staphylococus aureus* and *Pseudomonas aeruginosa*, and viruses such as hepatitis B and HIV, while at the same time being simple and straightforward enough to be accomplished with a minimum expenditure of time after the surgical instruments have been used, by personnel requiring a minimum amount of training, and using apparatus and materials which are both inexpensive and reliable. Moreover, it has typically been a problem that the surgical instruments and other paraphernalia may be grossly soiled, and therefore require vigorous cleaning in addition to initial decontamination. Unfortunately, compositions are not available which will accomplish both the vigorous cleaning of grossly soiled surgical instruments and their microbiological decontamination. This problem has been further augmented by the fact that cleaning and decontaminating compositions are usually incompatible for a variety of reasons. Thus, heretofore, it has not been possible to readily combine both the cleaning and decontaminating of surgical instruments into an efficient method.

2. Brief Description of the Prior Art

A number of different methods are known in the art for disinfecting or decontaminating surgical instruments and other medical paraphernalia. See, e.g., Bertil Nystrom, 1981 *Journal of Hospital Infection*, 2, 363–368.

Mild cleaning and disinfecting products are known in the art, e.g., germicidal detergents such as a phenolic-based disinfectant. However, it has not been known or suggested that such germicidal detergents be combined with more vigorous cleaning agents such as enzyme-based presoaks for medical apparatuses and instruments. In the literature for such an enzyme-based presoak, it is usually recommended that any items requiring sterilization or disinfection should be treated in a separate subsequent step. Compatibility of such enzyme-based presoaks with strong disinfectants is also a recognized problem. For example, it is well known that anionic detergents deactivate protease enzymes.

For example, Thomasen U.S. Pat. No. 4,867,797 discloses a method for cleaning instruments used for analyzing protein-containing biological liquids which utilizes an enzyme rinse solution, but uses germicides therewith only in low concentrations and only to increase the stability of the enzyme composition by protecting it against microbial deterioration.

SUMMARY OF THE INVENTION

The present invention relates to a method of cleaning and microbiologically decontaminating substantially soiled surgical instruments, comprising the following two steps carried out in the same container: (1) immersing substantially soiled surgical instruments in an enzyme-based cleaning composition for at least 5 minutes at room temperature, whereby substantially all materials soiling said instruments are removed; followed immediately by (2) adding to said container an amount of a germicidal detergent microbiological decontaminating composition sufficient to give a final concentration of at least 1 oz./gal. and continuing to immerse said instruments for at least an additional 5 minutes, whereby in addition to substantially all of the soil being removed, additionally substantially all of the microbiological contamination is removed from said surgical instruments.

The present invention further relates to the method of cleaning and microbiologically decontaminating substantially soiled surgical instruments described above in which the cleaning composition and the germicidal detergent microbiological decontaminating composition comprise the following materials:

| Ingredient | Percent by Weight |
|---|---|
| ENZYME-BASED CLEANING COMPOSITION | |
| Borax | 3.3 |
| Triethanol Amine | 12.5 |
| Propylene Glycol | 28.0 |
| Calcium Chloride | 0.1 |
| Citric Acid Anhydrous | 4.0 |
| Linear Alcohol Ethoxylate | 1.0 |
| Protease | 4.0 |
| Hydroxyethyl cellulose | 0.2 |
| Zeolite ® Softened Water | balance (46.9) |
| GERMICIDAL DETERGENT MICROBIOLOGICAL DECONTAMINATING COMPOSITION | |
| Caustic Potash (45% KOH) | 11.4 |
| Sodium Xylene Sulfonate | 4.0 |
| Caustic Soda (50% NaOH) | 3.0 |
| Para Tert-amyl Phenol | 7.8 |
| Phosphoric Acid (75%) | 3.7 |
| Ortho-phenylphenol | 9.2 |
| α-Olefin Sulfonate | 13.4 |
| Fragrance | 0.3 |

-continued

| Ingredient | Percent by Weight |
|---|---|
| ENZYME-BASED CLEANING COMPOSITION | |
| Zeolite ® Softened Water | balance (47.2) |

DETAILED DESCRIPTION OF THE INVENTION

The term "surgical instruments" as used herein means any of those instruments commonly used in a wide variety of surgical procedures, whether in a hospital operating room environment or in a doctor's office on an outpatient basis. Such instruments are, for the most part, made of surgical quality stainless steel, but they may be composed of other materials as well, e.g., aluminum and polypropylene and other polymer materials. In addition, the term "surgical instruments" includes other medical and surgical paraphernalia which might not properly be considered a surgical instrument, but which comes into contact with human tissue, especially blood, during a surgical or some other medical procedure, during the course of which that item of medical or surgical paraphernalia becomes grossly soiled and microbiologically contaminated. Examples of such medical and surgical paraphernalia are cardiovascular instruments, eye instruments, micro-surgical instruments, neurologic and orthopedic instruments, laparoscopes, flexible fiberoptic scopes, endoscopes, bronchoscopes, cystoscopes, and respiratory therapy equipment.

The terms "grossly soiled" and "substantially soiled" as used herein mean the condition of being contaminated to a substantial extent by contact with human tissue, fluids, excretia, and so forth, as the result of contact therewith during some surgical or other medical procedure. Contamination by contact with human blood in substantial amounts is particularly referred to, and this includes microbiological contamination by viruses and bacteria contained in that blood. A surgical instrument which is "grossly soiled" is one which requires a step of cleaning in addition to a step of decontamination, and is thus one which will benefit in particular from the method of the present invention. The step of cleaning removes the human tissue, fluids, excretia, etc. which have adhered to the surgical instrument, but provides little or no microbiological decontamination of the viruses, bacteria or other microorganisms present in that human tissue, fluids, excretia, etc., which have also adhered to the surgical instrument to be cleaned. For these, the further step of microbiological decontamination in accordance with the method of the present invention is required.

The term "enzyme-based cleaning composition" as used herein refers to cleaning compositions especially designed to remove substantially all human tissue, fluids, excretia, etc. from grossly soiled metal and other surfaces, especially surgical instruments and other medical paraphernalia, in which the enzyme is selected from protease, lipase, amylase, or other enzymes or combinations of enzymes and surfactants known to break down blood, body tissue and excretia.

The enzyme-based cleaning composition may have a number of additional ingredients which help promote its effectiveness and use, e.g., other cleaning agents such as sodium tetraborate, emulsifiers such as triethanolamine, solvent thickeners such as propylene glycol, acidifiers such as citric acid, buffering agents, preservatives, and so forth. Such excipients would be well known to one of ordinary skill in this art.

The balance of the enzyme-based cleaning composition comprises Zeolite® softened water, prepared by passing tap water through a Zeolite® sodium cation exchange column. Such Zeolite® softened water should have a pH in the range of from 9.0 to 10.0; a bacterial content of no more than 100 CFU/mL, preferably 0; a NaCl content of no more than 20 mg/L, preferably no more than 10 mg/L; an iron content of no more than 0.5 ppm, preferably no more than 0.1 ppm; and a total hardness as $CaCO_3$ of no more than 20 mg/L, preferably no more than 17.1 mg/L. Of these characteristics of the softened water used to make up the enzyme-based cleaning composition, the most important is the hardness.

In a preferred embodiment of the present invention, the enzyme-based cleaning composition has the following composition: protease, non-ionic detergent, propylene glycol, and sodium tetraborate and Zeolite® softened water.

The term "germicidal detergent microbiological decontamination composition" as used herein refers to germicidal detergents especially designed to provide microbiological decontamination of all grossly soiled metal and other surfaces, especially surgical instruments and other medical paraphernalia, selected from phenolic compounds, quaternary amines, glutaraldehyde and other known disinfectants or combinations thereof.

The disinfectant, i.e., the germicidal detergent decontaminating composition may have a number of additional ingredients which help promote its effectiveness and use, e.g., strong acids and bases such as phosphoric acid and caustic soda, emulsifiers and surfactants such as $\alpha$-olefin sulfonate, and various fragrances which help to mask the odor of the phenolic compounds.

The balance of the germicidal detergent decontaminating composition comprises Zeolite® softened water, prepared by passing tap water through a Zeolite® sodium cation exchange column. Such Zeolite® softened water should have a pH in the range of from 9.0 to 10.0; a bacterial content of no more than 100 CFU/mL, preferably 0; a NaCl content of no more than 20 mg/L, preferably no more than 10 mg/L; an iron content of no more than 0.5 ppm, preferably no more than 0.1 ppm; and a total hardness as $CaCO_3$ of no more than 20 mg/L, preferably no more than 17.1 mg/L. Of these characteristics of the softened water used to make up the germicidal detergent decontaminating composition, the most important is the hardness.

In a preferred embodiment of the present invention, the germicidal detergent decontaminating composition has the following makeup: phenol (carbolic acid), anionic detergent, phosphate builders and Zeolite® softened water.

It is a requirement, but in fact an advantage, of the method of the present invention, that the two steps thereof are carried out in the same container. Once the surgical instruments have been immersed in the bath of enzyme-based cleaning composition, which should be accomplished in such a way that the surgical instruments are completely immersed in said composition, the second step of microbiological decontamination is carried out simply by adding the germicidal detergent to that same container in sufficient amount that the concentration thereof is at least 1 oz./gal., with reference to the total volume now present in the container.

It will be appreciated that the enzyme-based cleaning composition must be compatible with the germicidal detergent decontaminating composition to the extent that the former should not degrade, destroy, inhibit or in any way impair the functioning of the latter. This one way compatibility, is, in fact, the opposite of that with which the art is usually concerned, i.e., the tendency of germicidal microbiological decontaminating compositions to inactivate or otherwise have some serious undesirable impact on the enzyme-based cleaning composition. Indeed, it is no impediment at all to carrying out the method of the present invention for the germicidal detergent microbiological decontaminating composition to be incompatible with the enzyme-based cleaning composition, in the sense that the former deactivates the latter. A problem only arises where the latter deactivates the former, a rare occurrence.

The length of time that each step takes has already been indicated as being at least 5 minutes. These minimum immersion times afford the minimum amount of acceptable cleaning and microbiological decontamination. However, longer times are usually desirable, and it is preferred that immersion times of about 20 minutes be utilized for each of the two steps. While longer times may be employed, they do not result in any significant improvement in the extent of cleaning and microbiological decontamination.

The method of the present invention is carried out at room temperature, which is a considerable advantage, since it requires no special provision for heating of the cleaning and/or microbiological decontamination compositions. Room temperature is usually regarded as 20° C., but the method of the present invention is carried out at ambient temperature, whatever that may happen to be. But, of course, temperatures significantly below room temperature will result in a reduced rate of cleaning and microbiological decontamination, requiring correspondingly longer immersion times for each step.

The method of the present invention may be carried out simply by immersing the grossly soiled surgical instruments in the container having the enzyme-based cleaning composition, to which is then added the germicidal detergent microbiological decontamination composition, without any accompanying agitation. However, it will be appreciated that the cleaning and decontamination steps can be accomplished more quickly and efficiently by employing agitation. Consequently, it is also part of the method of the present invention to carry out the steps thereof using agitation. Such agitation can be merely manual, or it may be accomplished by use of a mechanical agitating device by means of which the container in which the surgical instruments have been immersed is agitated.

EXAMPLE OF PREFERRED EMBODIMENT

The following example provides a detailed demonstration of a preferred embodiment of the method of the present invention, but is not intended to be in any way a limitation of the scope thereof.

Materials for Gross Soiling:

In order to prepare a contamination slurry, a ratio of 5 g of USDA grade A ground sirloin to 20 mL of defibrinated sheeps' blood was placed in a Waring Blender, and blended at high speed for about 2 min, after which the resulting slurry was removed and filtered twice through a sterile filter comprising two layers of 2×2 in$^2$. pieces of sterile gauze into sterile 25×150 mm test tubes. There was added an equal volume of a 48 hour culture (approximately $10^9$ organisms/mL.) of a microorganism selected from the following:

*Staphylococcus aureus* ATCC 6538;

*Pseudomonas aureus* ATCC 15442;

*Salmonella choleraesuis* ATCC 10708

Propagation of cultures of the above microorganisms and the use of subculture media and other related equipment were as specified in sections 4.001, 4.002, 4.007, 4.008 and 4.025 (Methods 1, 2, and 3) of the AOAC (Association of Official Analytical Chemists) Manual of Methods (14th ed.).

Soiling of Surgical Instruments:

To serve as "surgical instruments" there was used polished stainless steel cylinders (penicillin cups) 8±1 mm od, 6±1 mm id, length 10±1 mm of type 304 stainless steel SS 18-8. In order to produce gross soiling of the cylinders, there was used 3 mL of the contamination slurry to which was added 1 mL of the slurry for each cylinder in the test. Thus, for three cylinders, 6 mL of contamination slurry was used. Prior to contamination, the test cylinders were soaked overnight in 1N NaOH, after which they were rinsed with tap water until the rinse water was neutral to phenolphthalein, and then rinsed twice with distilled water. The cleaned cylinders were placed in groups of 10 to 30 and covered with distilled water, sterilized 20 min at 121° C., cooled, and held at room temperature.

To accomplish gross soiling, the required number of cylinders for the test were transferred into the appropriate amount of contamination slurry, and allowed to soak therein at room temperature for 15 min, with occasional gentle shaking to insure that all cylinders were in contact with the slurry. After the 15 min contact period, the liquid was decanted and the cylinders were removed and placed on end in vertical position in a sterile glass petri dish matted with filter paper, covered, and dried in an incubator at 35°±1° C. for 30 min. The cylinders were transferred using a suitable wire sterilized by flame.

Cleaning Step:

The dried cylinders were removed from the petri dish and placed in a sterilized test tube, five cylinders per test tube, to which was then added 10 mL of a enzyme-based cleaning composition containing the following ingredients:

| Ingredient | Percent by Weight |
| --- | --- |
| Borax | 3.3 |
| Triethanol Amine | 12.5 |
| Propylene Glycol | 28.0 |
| Calcium Chloride | 0.1 |
| Citric Acid Anhydrous | 4.0 |
| Linear Alcohol Ethoxylate | 1.0 |
| Protease | 4.0 |
| Hydroxyethyl cellulose | 0.2 |
| Zeolite ® Softened Water | balance (46.9) |

The cleaning composition was diluted to a use concentration of 2 oz/gal using 400 ppm hard water (prepared according to 4.027 Method 3 of AOAC Manual of Methods, 14th ed., to the desired hardness of 400 ppm), and was maintained at 25° C. for 20 min.

Microbiological Decontamination Step:

At the end of the 20 min cleaning contact time, there was added to the test tube containing the cylinders and 10 mL of diluted cleaning composition, 0.16 mL of concentrated germicidal detergent microbiological decontamination composition containing the following ingredients:

| Ingredient | Percent by Weight |
| --- | --- |
| Caustic Potash (45% KOH) | 11.4 |
| Sodium Xylene Sulfonate | 4.0 |
| Caustic Soda (50% NaOH) | 3.0 |
| Para Tert-amyl Phenol | 7.8 |
| Phosphoric Acid (75%) | 3.7 |
| Ortho-phenylphenol | 9.2 |
| α-Olefin Sulfonate | 13.4 |
| Fragrance | 0.3 |
| Zeolite ® Softened Water | balance (47.2) | which resulted in an overall concentration of 2 oz/gal. A contact time of 20 min was allowed for this decontamination step, after which the test tube was shaken.

each of two different batches of cleaning and disinfectant compositions used, for each microorganism. The results of these tests are summarized in the table of data below.

TABLE 1

Cleaning and Decontamination of Grossly Soiled Surgical Instruments

| TEST SYSTEM | Organism | Phenol Res.* | Plate Count | Cylinder* |
|---|---|---|---|---|
| Enzyme System 2 oz/gal. + Disinfectant 2 oz/gal. | S.A. | 1:50 | <10 | 0/120 |
| Enzyme System 2 oz/gal. | S.A. | 1:50 | 7.2E + 05 | 20/20 |
| Disinfectant 2 oz/gal. | S.A. | 1:50 | <10 | 1/20 |
| Control (dried cylinder count) | S.A. | 1:50 | 9.5E + 05 | 20/20 |
| Enzyme System 2 oz/gal. + Disinfectant 2 oz/gal. | P.A. | 1:80 | <10 | 0/120 |
| Enzyme System 2 oz/gal. | P.A. | 1:80 | 2.3E + 06 | 15/15 |
| Disinfectant 2 oz/gal. | P.A. | 1:80 | <10 | 4/15 |
| Control (dried cylinder count) | P.A. | 1:80 | 3.2E + 06 | 15/15 |
| Enzyme System 2 oz/gal. + Disinfectant 2 oz/gal. | S.C. | 1:80 | <10 | 0/120 |
| Enzyme System 2 oz/gal. | S.C. | 1:80 | 1.0E + 05 | 10/10 |
| Disinfectant 2 oz/gal. | S.C. | 1:80 | <10 | 2/10 |
| Control (dried cylinder count) | S.C. | 1:80 | 1.1E + 05 | 10/10 |

Test organisms: S.A. = *STAPHYLOCOCCUS AUREUS* ATCC 6538, P.A. = *PSEUDOMONAS AERUGINOSA* ATCC 15442
S.C. = *SALMONELTA CHOLERAESUIS* ATCC 10708
The test was run in 400 ppm hard water
Total test time 40 minutes: 20 minutes Enzyme System @25 C. then 20 minutes Disinfectant @25 C..
All cylinders were prepared and inoculated according to test procedure. Drying time 30 min.
Subculture media was Fluid Thioglycolate with Lecithin and Tween.
Gross soiling is carried out as per procedure.
*Cylinder = the number of positive cylinders over the total number of cylinders tested.
Phenol resistance is determined as per the AOAC test method.

Evaluation:

After shaking the test tube, 2.5 mL of liquid was removed, 1 mL of which was placed in a test tube containing 9 mL of FTLT neutralizing media (fluid thioglycollate with lecithin and polysorbate emulsifier (Tween®), per 4.001 (d)(5) of AOAC Manual of Methods, 14th ed.). The mixture was stirred with a vortex, and 2.5 mL was removed, a first 1 mL of which was placed in a petri dish and labeled $10^1$; and a second 1 mL sample of which was added to another test tube containing 9 mL of FTLT, vortexed and a 1 mL sample removed to make the $10^2$ dilution. This procedure was repeated to give $10^1$–$10^5$ samples.

Agar plates containing 15–20 mL of plate count agar were then poured, allowed to cool, inverted, and incubated at 30° C. for 48 hrs. The plate count agar was obtained from Difco Laboratories, Detroit, Mich., 23.5 g of which was rehydrated in 1 L of distilled water, mixed thoroughly and autoclaved for 15–20 min at 121° C. to achieve sterilization as per label instructions. The number of colony forming units (CFU's) on the agar plates was counted either manually or using appropriate automated equipment.

The test tubes containing the test cylinders were shaken and all of the cylinders removed at the time the last sample was taken, as described above. Each cylinder was placed in a test tube containing approximately 10 mL of the FTLT neutralizing media, after which the tube was shaken and incubated at 35°±1° C. for 48 hrs. Each tube was then recorded either as positive, indicating growth, or negative, indicating no growth.

Tests parallel to those described above were run on the first step, second step, and hardwater blank contaminated cylinders as controls.

The phenol resistance of all of the above cultures was determined in accordance with AOAC 4.001–4.006. The results of the active formulations combinations showed no growth in the plate count procedure and no growth in the FTLT subculture media after the 20 min contact time with the second step microbiological decontamination. A total of 10 replicates were done for the second step procedure for

What is claimed is:

1. A method of cleaning and microbiologically decontaminating substantially soiled surgical instruments, comprising the following two steps carried out in the same container: (1) immersing substantially soiled surgical instruments in an enzyme-based cleaning composition for at least 5 minutes at room temperature, whereby substantially all materials soiling said surgical instruments are removed; followed immediately by (2) adding to said container an amount of a germicidal detergent microbiological decontaminating composition sufficient to give a final concentration thereof of at least 1 oz./gal. and continuing to immerse said surgical instruments for at least an additional 5 minutes.

2. The method of cleaning and microbiologically decontaminating substantially soiled surgical instruments of claim 1 in which the enzyme-based cleaning composition and the germicidal detergent microbiological decontaminating composition respectively comprise the following:

| Ingredient | Percent by Weight |
|---|---|
| Borax | 3.3 |
| Triethanol Amine | 12.5 |
| Propylene Glycol | 28.0 |
| Calcium Chloride | 0.1 |
| Citric Acid Anhydrous | 4.0 |
| Linear Alcohol Ethoxylate | 1.0 |
| Protease | 4.0 |
| Hydroxyethyl cellulose | 0.2 |
| Zeolite ® Softened Water | balance (46.9) |
| Caustic Potash (45% KOH) | 11.4 |
| Sodium Xylene Sulfonate | 4.0 |
| Caustic Soda (50% NaOH) | 3.0 |
| Para Tert-amyl Phenol | |
| Phosphoric Acid (75%) | 7.8 |
| Ortho-phenylphenol | 3.7 |
| α-Olefin Sulfonate | 9.2 |
| Fragrance | 13.4 |
| Zeolite ® Softened Water | balance [(@47.2)] (47.2) |

3. The method of cleaning and microbiologically decontaminating substantially soiled surgical instruments of claim 1 in which immersion times for each step is 20 minutes.

4. The method of cleaning and microbiologically decontaminating substantially soiled surgical instruments of claim 2 wherein the concentration of both the cleaning and decontaminating compositions is 2 oz/gal.

* * * * *